United States Patent [19]

Suzuki et al.

[11] Patent Number: 5,555,898
[45] Date of Patent: Sep. 17, 1996

[54] GASTRIC ACCESS DEVICE

[75] Inventors: Yutaka Suzuki, Chiba; Hideyuki Kashiwagi, Tokyo; Teruaki Aoki, Tokyo; Fumiichi Koshino, Tokyo, all of Japan; George J. Picha, Independence; Anthony J. Szpak, Parma, both of Ohio

[73] Assignee: Applied Medical Research, Inc., Independence, Ohio

[21] Appl. No.: 311,918

[22] Filed: Sep. 26, 1994

[51] Int. Cl.$^6$ .................................................. A61B 19/00
[52] U.S. Cl. ............................................ 128/898; 604/171
[58] Field of Search ............................ 128/897–99, 774, 128/280; 604/54, 171, 175, 104–109

[56] References Cited

U.S. PATENT DOCUMENTS

| | | |
|---|---|---|
| 4,863,438 | 9/1989 | Gauderer et al. . |
| 5,084,014 | 1/1992 | Picha et al. . |
| 5,343,874 | 9/1994 | Picha et al. . |
| 5,356,382 | 10/1994 | Picha et al. ............................ 604/105 |

*Primary Examiner*—Angela D. Sykes
*Assistant Examiner*—John P. Lacyk
*Attorney, Agent, or Firm*—Pearne, Gordon, McCoy & Granger

[57] ABSTRACT

A gastric access device having an external bolster and a tubular body. The tubular body has an integral bolster portion at one end and an integral dilator portion at an opposite end. An incision extending from an external body surface to an internal body cavity is formed and the gastric access device is inserted through the incision such that the bolster portion is in contact with an inner body surface surrounding the internal body cavity, the tubular body lies within and projects outwardly from the incision, and the dilator portion is on the outside or exterior of the body. The external bolster is slid or pushed down over the dilator portion and the projecting portion of the tubular body and into contact with the external surface of the body. The projecting portion of the tubular body is clamped and subsequently severed to disconnect the dilator portion from the tubular body. Thereafter, air flow control devices may be inserted into the tubular body, and surgical tools inserted through the tubular body and into the internal body cavity. The surgical tools are manipulated by the surgeon to perform surgical procedures on the tissue within the internal body cavity.

16 Claims, 4 Drawing Sheets

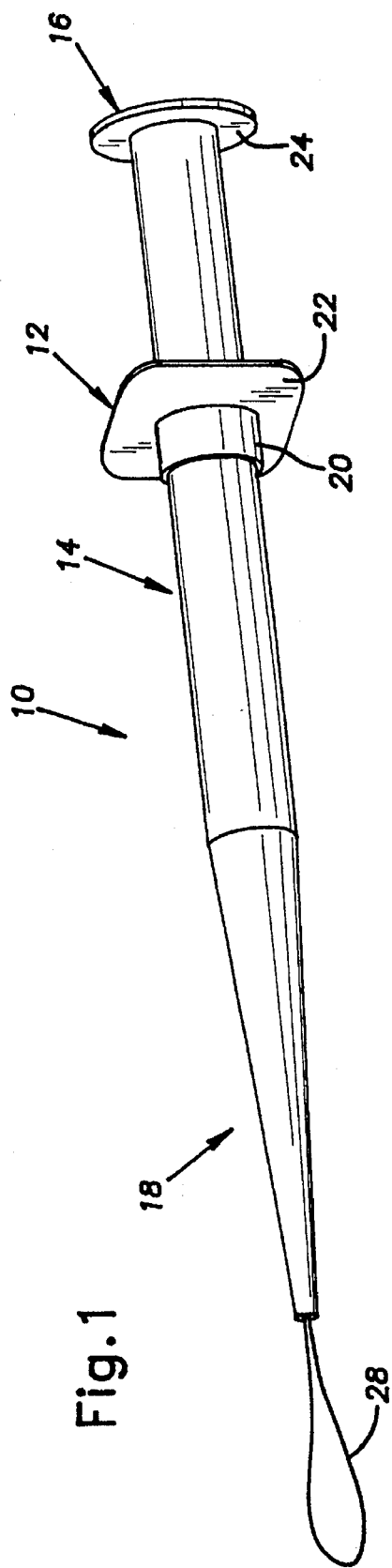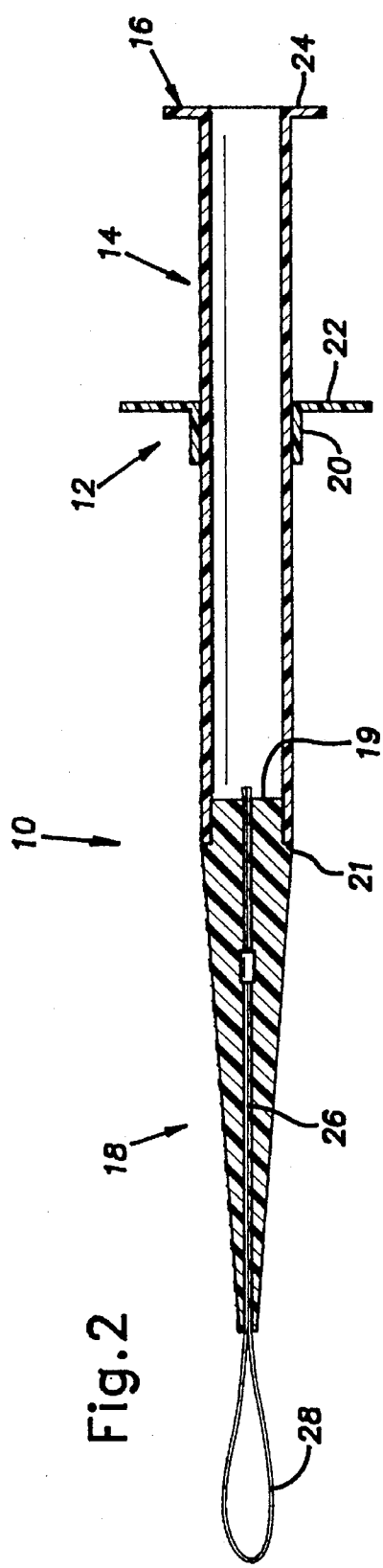
Fig.1
Fig.2

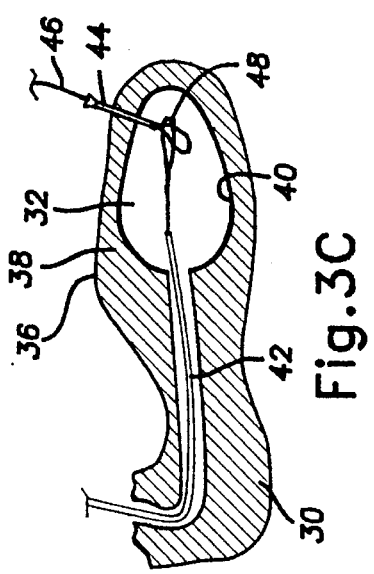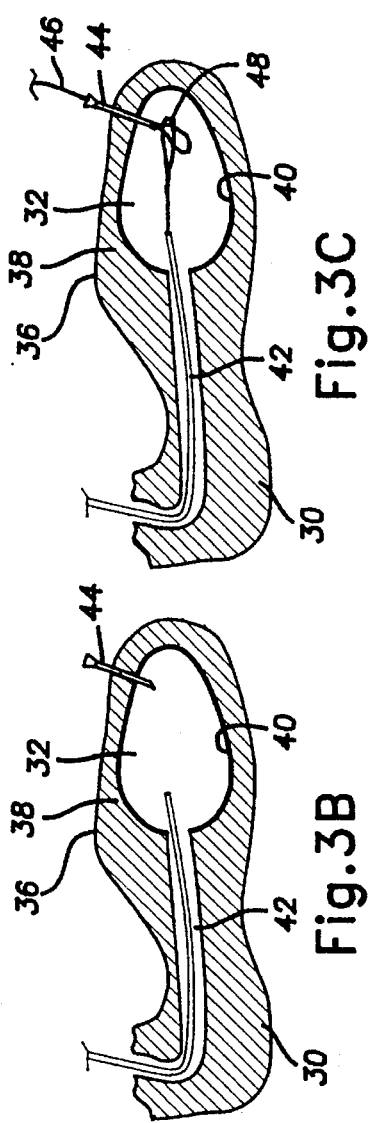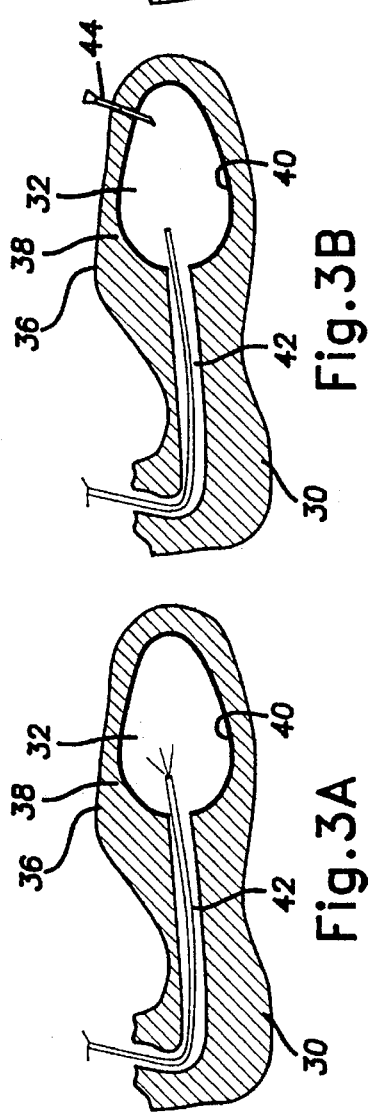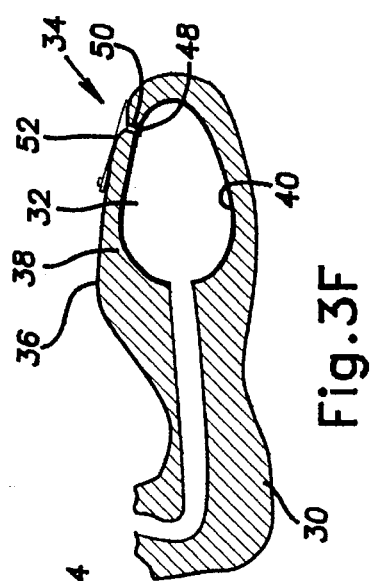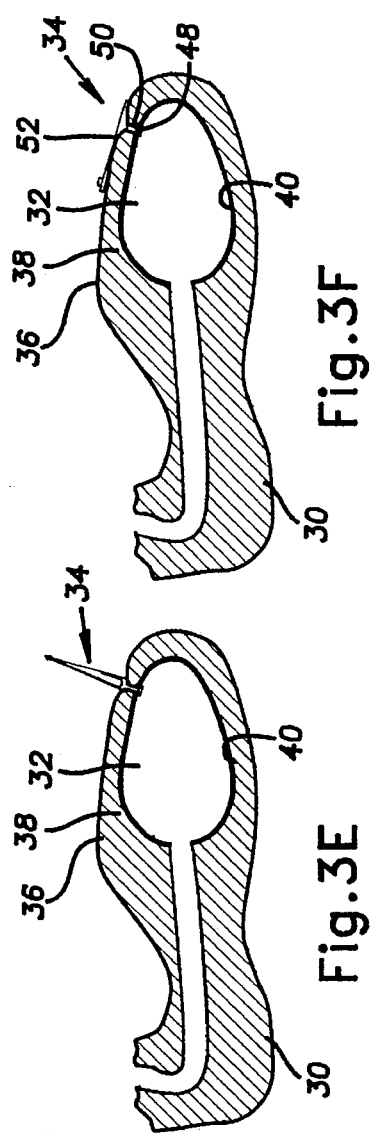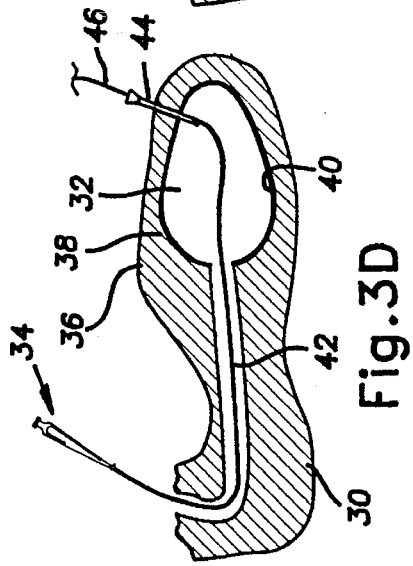

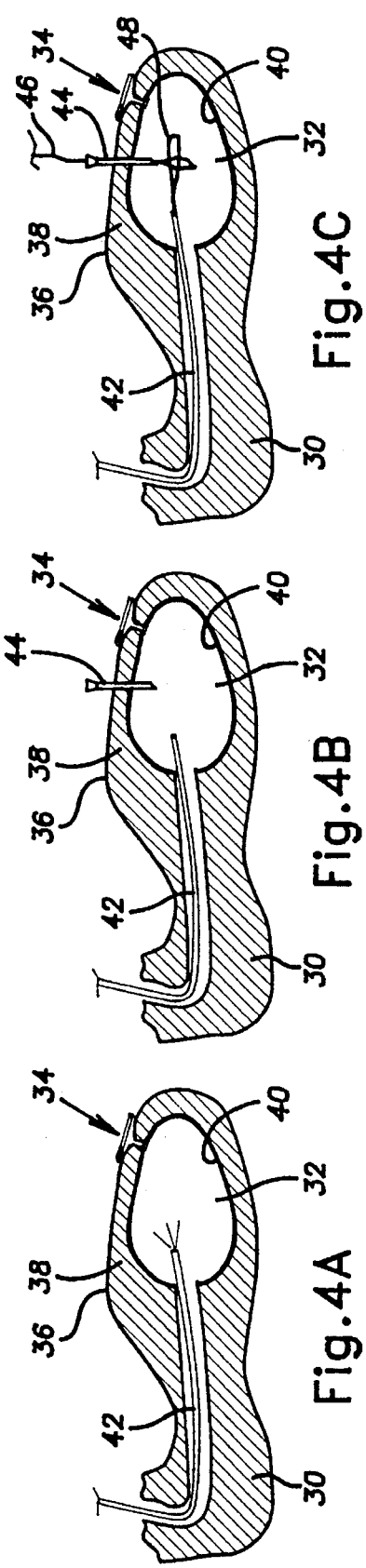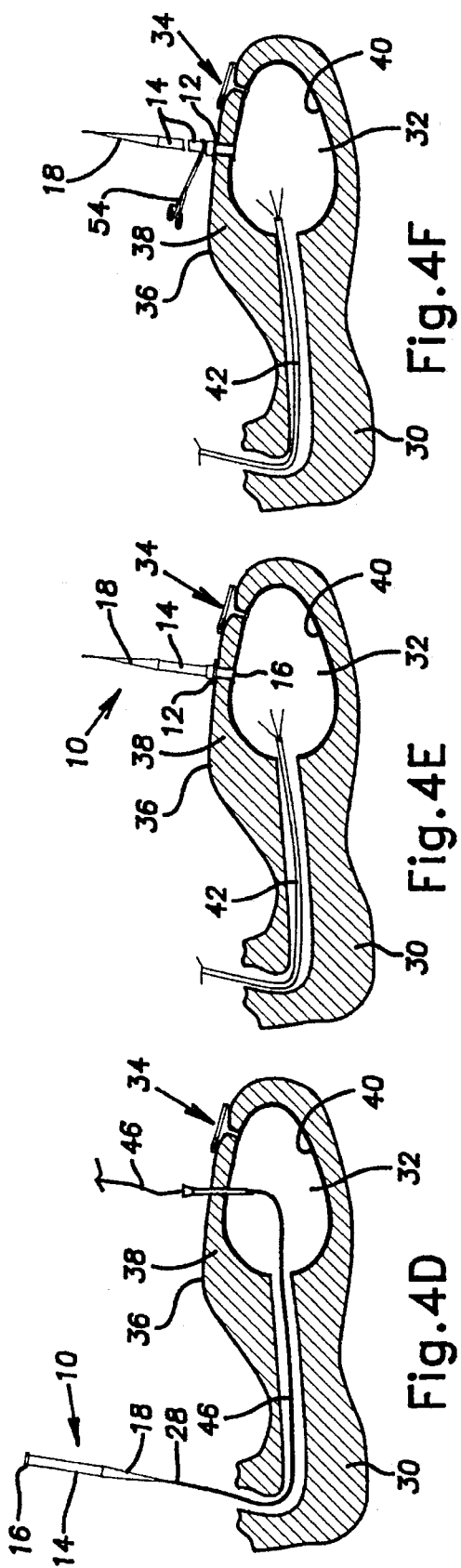

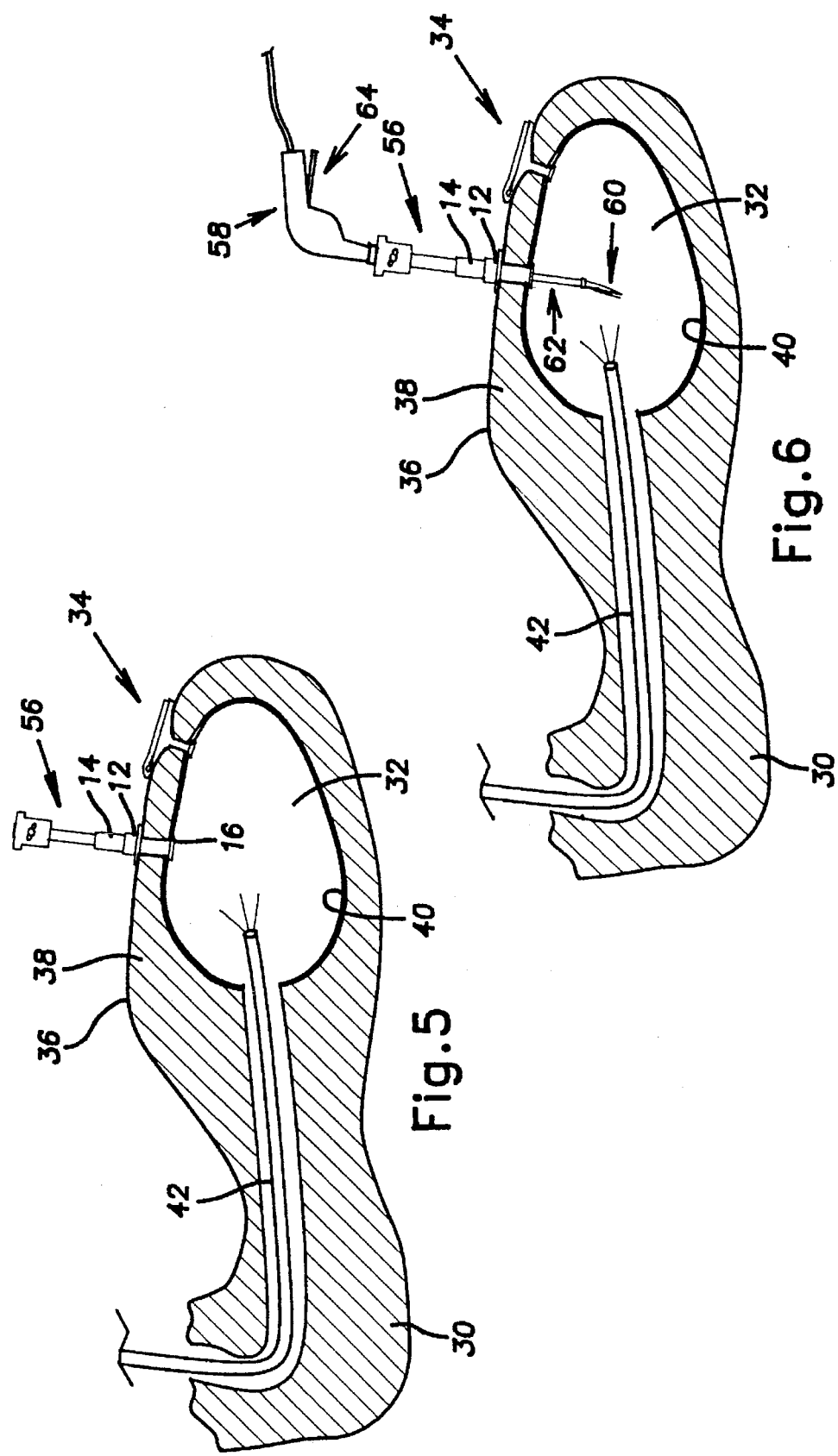

5,555,898

GASTRIC ACCESS DEVICE

BACKGROUND OF THE INVENTION

The present invention generally relates to surgical devices and methods and, more particularly, to surgical devices specifically adapted for percutaneous surgical procedures and to methods for performing percutaneous surgical procedures.

Endoscopic surgery, and surgery made possible through the remote visualization provided by endoscopes, has developed dramatically in recent years and offers many advantages over more traditional surgical procedures. One of the major limitations of endoscope-assisted surgery and any surgery in which surgical instruments are inserted through the skin to an interior surgical site, is the formation and maintenance of a proper entry port in the skin and underlying tissue layers. In many surgical procedures, such as gastric surgery and others wherein the organ or tissue to be worked upon must be insufflated, the entry port must minimize leakage of pressurizing air. Prior to the present invention, no reliable device or method for the formation and maintenance of a surgical entry port has been available, thereby rendering endoscopic surgery impractical as a replacement for traditional "open wound" type surgical procedures.

SUMMARY OF THE INVENTION

The present invention provides an improved percutaneous surgery entry port device, a method for the formation of an entry port for percutaneous surgery, and an improved percutaneous surgical procedure or method. In accordance with the present invention, an entry port device includes an external bolster and a generally cylindrical or tubular body. The tubular body has a bolster portion at one end and a dilator portion at an opposite end. The dilator portion preferably includes an integral pull line. Alternatively, the dilator portion may have a central bore through which a guide or pull wire is fed to assist in passing of the device through a previously formed incision.

In further accordance with the present invention, a method of using or installing an entry port device of the above-noted type includes the steps of forming an incision extending from an external surface of a living body to an internal body cavity, such as a stomach, positioning the entry port device within the internal body cavity, inserting the dilator portion through the incision such that the cylindrical or tubular body lies within the incision and projects outwardly therefrom and the bolster portion remains within the internal body cavity and is adjacent a surface surrounding the internal body cavity, sliding an external bolster over the dilator portion and the exposed portion of the tubular body and against the external surface of the living body, removing the dilator portion from the tubular body, and inserting a surgical instrument through the tubular body and into the internal cavity. In practicing the method of placing the device, the dilator portion can be either pulled or pushed through the incision depending upon the type of dilator portion utilized, as noted above.

In accordance with the present invention, the entry port device, once installed within the patient's body, forms a stable entry port for percutaneous surgical procedures. Surgical tools are inserted into the stomach via the tubular body and, once therein, are manipulated by the surgeon to remove or repair tissue, as desired.

BRIEF DESCRIPTION OF THE DRAWINGS

These and further features of the present invention will be apparent with reference to the following description and drawings, wherein:

FIG. 1 is a perspective view of a preferred embodiment of a percutaneous surgery entry port device according to the present invention;

FIG. 2 is an elevational view, in cross section, of the entry port device of FIG. 1;

FIGS. 3A–3F sequentially illustrate the methodology for placing a modified gastrostomy device in an incision in a living body;

FIGS. 4A–4F sequentially illustrate the methodology for placing the entry port device of FIGS. 1–2 in an incision in a living body in accordance with the present invention;

FIG. 5 illustrates an air flow control device placed in the entry port device installed in FIGS. 3A–4F; and FIG. 6 illustrates a surgical tool extending through the air flow control device of FIG. 5, for performing a surgical procedure within the living body.

DETAILED DESCRIPTION OF THE DRAWINGS

A percutaneous entry port device 10 according to the present invention, as shown best in FIGS. 1 and 2, includes a removable external bolster 12 and a cylindrical or tubular body 14. Preferably, the external bolster 12 and the tubular member 14 are made from polyurethane.

The tubular body 14 has a bolster portion 16 integrally attached thereto at one end and a dilator portion 18 integrally attached thereto at an opposite end. As used herein, the term "integrally attached" refers to either a unitary or one-piece structure or to a structure in which separately formed pieces are subsequently attached to form a unitary structure. In the present invention, for example, the tubular body 14 and bolster portion 16 are preferably integrally molded in one piece, while the dilator portion 18 is formed separately and subsequently attached to the tubular body by appropriate adhesives or, optionally, fasteners. Naturally, it is contemplated that the tubular body 14, dilator portion 18, and bolster portion 16 could be formed or molded in one piece, or could all be separately formed and thereafter attached to one another by conventional fasteners or adhesives. Moreover, it is contemplated that the dilator portion 18 and tubular body 14 could be integrally molded in one piece and subsequently attached by conventional fasteners or adhesives to a separately formed bolster portion 16. Therefore, the term "integrally attached" is intended to cover all of these types of construction and assembly, as well as any equivalents thereto, without departing from the scope and spirit of the present invention as defined in the claims appended hereto.

The external bolster 12 includes a cylindrical portion 20 which surrounds the tubular body 14 and is slidably movable therealong. A rim or collar 22 extends radially outwardly from the cylindrical portion 20 and, in use, is positioned against an external body surface. As will be discussed more fully hereafter, the external bolster 12 is positioned against the external body surface by sliding the external bolster over and down the tubular body 14, and may be attached or secured to the tubular body 14 by means of sutures or equivalent mechanical fastening means.

The tubular body 14 is preferably hollow, and the bolster portion 16 provides a sealing ring or stop 24 which extends radially outwardly therefrom. The dilator portion 18 is co-axial with the tubular body 14 and gradually reduces in diameter as it extends away from the tubular body 14, as illustrated. The dilator portion 18 has a proximal end 19 which extends into the tubular body 14 a short distance and is adhesively secured thereto. An annular rim 21 provided by the proximal end 19 abuts an end of the tubular body 14 and provides a smooth transition between the tubular body 14 and the dilator portion 18.

Preferably, a pull line 26 is integrally formed or molded into the dilator portion 18. The pull line 26 has a looped, exposed end 28 which projects outwardly from the dilator portion 18, as illustrated, which can be tied to another pull line or guide wire to assist in installation of the entry port device 10, as will be discussed more fully hereafter.

Alternatively, the dilator portion 18 can be more elongated and provide a central bore or passageway instead of the pull line. An elongated dilator portion with a central passageway would allow the device to be pushed on over a guide wire, as is generally well-known in the art. Such a dilator construction is illustrated in U.S. Pat. No. 5,084,014, the disclosure of which is expressly incorporated herein by reference.

The tubular body 14 has a length dimension in excess of the tissue thickness to be penetrated to allow the tubular body 14 to extend through and project out of an incision or incised tract. The sealing ring 24 provided by the bolster portion 16 is dimensioned to prevent the entry port device 10 from being unintentionally withdrawn or pulled through the incision. The sealing ring 24 cooperates with an inner surface defining an internal body cavity to provide a generally air-tight seal which prevents pressurizing air within the internal body cavity from leaking or flowing out through the incision. The internal diameter of the tubular body 14 is sufficient to allow surgical instruments to be inserted and removed therethrough, as will be apparent from the discussion to follow. Therefore, the diameter of the tubular body 14 will vary depending upon the surgical procedure to be performed and, more specifically, the size of the surgical instrument to be inserted therethrough.

In performing the method of the present invention, it is desirable to provide two access or entry ports. Preferably, one entry port is provided by a gastrostomy device generally of the type illustrated and disclosed in the '014 patent, and the second entry port is provided by the entry port device 10 of the present invention illustrated in FIGS. 1 and 2 and described hereinbefore. The gastrostomy device illustrated in FIGS. 3A–6 is generally of the type disclosed in the '014 patent and in U.S. Pat. No. 4,863,438, the disclosure of which is expressly incorporated herein in its entirety. However, the illustrated gastrostomy device differs from that of the '014 and '438 patents in that the illustrated device does not have a dome portion overlying the flapper valve. In the illustrated gastrostomy device (hereafter referred to as the "modified gastrostomy device"), the dome portion is removed to permit a surgical tool to pass through the modified gastrostomy device and into the internal body cavity. Reference should be made to the '014 and '438 patents for a more complete understanding of the gastrostomy device, which does not form a part of the present invention.

The modified gastrostomy device can be left in place for subsequent direct feeding of the patient, if necessary. If the modified gastrostomy device is to be left in place for subsequent direct feeding, the length of the incision or incised tract should be measured and an appropriately sized modified gastrostomy device installed therein, as is generally well known in the art. Measurement of the incision length could be provided by using the devices and methods disclosed in U.S. Pat. No. 5,343,874 or U.S. patent application Ser. No. 07/965,219, the disclosures of which are expressly incorporated herein by reference in their entirety. Naturally, if direct feeding of the patient is not necessary, it is contemplated that both ports could be provided by appropriately sized entry port devices 10 according to the present invention.

With reference to FIGS. 3A–3F, the method of placing in a patient a modified gastrostomy device will now be set forth. Turning to FIG. 3A, there is schematically illustrated a patient 30 having an inner body cavity, such as a stomach 32, within which is to be placed a modified gastrostomy device 34. It is to be noted that the modified gastrostomy device 34 and the entry port device 10 and percutaneous surgical method disclosed herein can be used in other areas of the body for other surgical procedures, such as, for example, urinary bladder procedures, ileostomy, jejunostomy, and cystostomy.

The external body surface or skin 36 of the patient 30 extends over an abdominal wall 38 which, in turn, abuts the stomach wall 40. In a first step for placing the modified gastrostomy device 34, the stomach 32 of the patient 30 is insufflated by pressurized air introduced therein via an endoscope tube 42 extending down through the esophagus of the patient, as illustrated. As illustrated in FIG. 3B, a conventional trocar 44 needle is inserted through the abdominal and stomach walls 38, 40 of the patient to establish an incision from the external body surface 36 to the internal body cavity or stomach 32 upon which the surgical procedure is to be performed.

As shown in FIG. 3C, a pull wire 46 is inserted down through the trocar needle 44 so that an end of the pull wire 46 can be captured by a snare 48 extending through the endoscope tube 42.

With further reference to FIG. 3D, the pull wire 46 has been pulled outwardly through the patient's mouth so that a pull wire of the modified gastrostomy device 34 can be attached, as illustrated.

Turning to FIG. 3E, the modified gastrostomy device 34, by use of the pull wire 46, has been pulled down through the esophagus of the patient 30, and then through the incision provided by the trocar needle 44.

Turning to FIG. 3F, an intra-gastric portion 48 of the modified gastrostomy device 34 is now located within the stomach 32 of the patient while a tubular mid-portion 50 extends through the abdominal and stomach walls 38, 40, with external wing-like projections 52 in their extended, uncollapsed, normal position engaging the skin 36 covering the abdominal wall 38, wherein the modified gastrostomy device 34 is now retained in position. The intra-gastric portion 48 includes an internal bolster which is in contact with the stomach wall 40 of the patient and a flapper valve (not shown) which prevents pressurized air from escaping through the tubular mid-portion 50 of the modified gastrostomy device 34. The modified gastrostomy device 34 so installed or positioned provides one port for access into the internal body cavity or stomach 32. The second port for access to the internal body cavity will hereafter be described with reference to FIGS. 4A–4F.

FIG. 4A illustrates a patient 30 having the modified gastrostomy device or button 34 installed as discussed above, and with the stomach 32 insufflated by means of the endoscope tube 42. Thereafter, as shown in FIG. 4B, a conventional trocar needle 44 is inserted through the abdominal and stomach walls 38, 40 of the patient to establish a second incision from the external body surface 36 to the internal body cavity or stomach 32 upon which the surgical procedure is to be performed.

As shown in FIG. 4C, a pull wire 46 is inserted down through the trocar needle 44 so that an end of the pull wire can be captured by a snare 48 extending through the endoscope tube 42.

With further reference to FIG. 4D, the pull wire 46 has been pulled outwardly through the patient's mouth so that the pull wire 28 projecting from the entry port device 10 (FIGS. 1 and 2) can be attached thereto, as illustrated.

Turning to FIG. 4E, the entry port device 10 of the present invention, by use of the pull wire 46, has been pulled down through the esophagus of the patient 30, and then through the incision provided by the trocar needle 44. At this point, the tubular portion 14 lies within and projects from the incision, while the sealing ring 24 of the bolster portion 16 is adjacent the stomach wall 32 surrounding the incision. The external bolster 12 has been slid or pushed down over the dilator portion 18 and the exposed or outwardly projecting portion of the tubular body 14, and is in contact with the external surface or skin 36 of the patient. The external bolster 12 may be sutured to the tubular body 14 to retain the external bolster 12 in position during the subsequent surgical procedure. Since the polyurethane from which the external bolster 12 and tubular body 14 are formed resists tearing, damage to the entry port device 10 caused by suturing is not a concern.

As so positioned, the sealing ring 24 provided by the bolster portion 16 is in engagement with the stomach wall 40 and cooperates therewith to form a generally air-tight seal to prevent pressurizing air from leaking or flowing into and through the incision.

At this point, as illustrated in FIG. 4F, the projecting portion of the tubular body 14 is clamped adjacent the external bolster 12 by a convention clamp 54, and the projecting portion is cut or severed to remove the dilator portion 18 therefrom. Thereafter, the clamp 54 is removed and an air flow control device 56 is inserted into the tubular body 14 to prevent leakage of pressurizing air therethrough, as illustrated in FIG. 5. The air flow control device 56 provides a central bore through which surgical tools may be inserted while generally preventing or minimizing loss of pressurizing air. One type of air flow control device 56 successfully used by the inventors of the present invention is sold under the tradename "ENDOPATH" by Ethicon, Inc.

FIG. 6 illustrates a surgical tool 58 inserted through the entry port device 10 of the present invention. The surgical tool 58 includes a tissue engaging portion 60 located within the internal body cavity or stomach 32, a shaft portion 62 extending through the tubular body 14 and air flow control device 54, and a user engageable portion 64. Manipulation of the user-engageable portion 64 is transmitted or communicated via the shaft portion 62 to the tissue engaging portion 62 and allows the surgeon to remotely perform surgical procedures on tissue within the internal body cavity 32.

Typically, one surgical tool is inserted into the stomach 32 through the modified gastrostomy device 34 and another surgical tool is inserted into the stomach 32 through the entry port device 10. One surgical tool grips or holds the tissue to be removed and one severs or cuts the tissue to be removed. Once the tissue is severed, the gripping tool is withdrawn from the entry port device 10 or modified gastrostomy device 34 to remove the severed tissue from the internal body cavity or stomach 32. The endoscope tube 42 remains within the internal body cavity and provides pressurizing air thereto and allows for remote visualization of the surgical site and surgical procedure by the surgeon. Several types of surgical tools are presently commercially available which have use in the present method. One such surgical tool is sold under the tradename "ENDOCUTTER" by Ethicon, Inc.

Following the procedure, the entry port device 10 may be removed from the incision by taking the external bolster 12 off the exposed portion of the tubular body 14, severing the tubular body 14 and bolster portion 16, radially collapsing the tubular body 14, and pulling the tubular body out of the incision. Alternatively, the tubular body 14 can be pushed into the internal body cavity and withdrawn therefrom via the esophagus by grasping means carried by the endoscope tube 42. According to another alternative, the bolster portion 16 may be severed from the tubular body 14 by means of a tool carried by the endoscope 42 and removed from the stomach 32 via the esophagus while the tubular portion 14 is simply pulled outwardly through the incision. Naturally, other alternative means to remove the tubular body 14 from the incision may be employed without departing from the scope and spirit of the present invention as defined by the claims appended hereto.

While the preferred embodiment of the present invention is shown and described herein, it is to be understood that the same is not so limited but shall cover and include any and all modifications thereof which fall within the purview of the invention. For example, it is contemplated that the tubular body 14 could be modified to have an end adjacent the dilator portion 18 which gradually reduces in diameter, generally at the same rate as the dilator portion, so that there is an even more smooth transition between the tubular body and the dilator portion. Moreover, although it is disclosed herein that two entry or access ports are formed to provide access into the internal body cavity, it is clearly contemplated that three or more access ports, some or all of which are formed by the device 10 of the present invention, could be provided as dictated by the surgical procedure to be performed.

What is claimed is:

1. A method for performing percutaneous surgery on a body, comprising the steps of:

forming an incision extending from an external surface of the body to an internal body cavity;

positioning within said cavity an entry port device having a tubular body, said tubular body having a bolster portion at one end and a dilator portion at an opposite end;

inserting said dilator portion into and through said incision whereby said tubular body extends through and projects from said incision and said bolster portion remains within said internal body cavity, said bolster portion preventing said device from unintentionally passing through said incision;

sliding an external bolster over said dilator portion and an exposed portion of said tubular body and in contact with said external surface;

severing said exposed portion of said tubular body to thereby remove said dilator portion from said tubular body;

inserting a surgical instrument through said tubular body and into said internal body cavity;

manipulating said surgical instrument to thereby perform a surgical procedure within said internal body cavity.

2. A method for performing percutaneous surgery as recited in claim 1, further comprising the steps of:

insufflating the internal body cavity with pressurized air; and, inserting an air flow control device into said tubular body to minimize leakage of pressurizing air through said tubular body.

3. A method for performing percutaneous surgery as recited in claim 2, comprising the further steps of:

inserting an endoscope tube into the internal body cavity; and, remotely visualizing the surgical procedure being performed via the endoscope tube.

4. A method for performing percutaneous surgery as recited in claim 1, comprising the further steps of:

severing tissue with said surgical instrument; and, removing said severed tissue from said internal body cavity via said tubular body.

5. A method for performing percutaneous surgery on a body, comprising the steps of:

insufflating an internal body cavity;

forming an incision extending from an external body surface to said internal body cavity;

positioning an entry port device within said internal body cavity, said device having a tubular body with a bolster portion at one end and a dilator portion at an opposite end;

inserting said dilator portion into and through said incision such that said dilator portion is on an exterior of the body, said tubular body having a portion which lies within said incision and a portion which projects outwardly from said incision while said bolster portion is in contact with an inner body surface surrounding said internal body cavity;

sliding an external bolster over said tubular body and against said external body surface;

severing said tubular body at a location adjacent said dilator portion;

inserting a surgical instrument through said tubular body and into said internal body cavity, said surgical instrument having a tissue engaging portion within said internal body cavity and a user engageable portion projecting outwardly from said tubular body;

adjusting said user engageable portion to manipulate said tissue engaging portion and thereby perform a surgical procedure within said internal body cavity.

6. A method for performing percutaneous surgery as recited in claim 5, further comprising the step of:

using a clamp to constrict a projecting portion of the tubular body to prevent pressurized air within said internal body cavity from flowing through said tubular body to atmosphere.

7. A method for performing percutaneous surgery as recited in claim 6, further comprising the steps of:

removing said clamp from the projecting portion of the tubular body; and, inserting an air flow control device into said tubular body to minimize leakage of pressurizing air through said tubular body.

8. A method for performing percutaneous surgery as recited in claim 7, further comprising the steps of:

inserting an endoscope tube into the internal body cavity; and, remotely visualizing the surgical procedure being performed via the endoscope tube.

9. A method for performing percutaneous surgery as recited in claim 8, comprising the further steps of:

severing tissue with said surgical instrument; and, removing said severed tissue from said internal body cavity via said tubular body.

10. A method for performing percutaneous surgery as recited in claim 5, comprising the further steps of:

severing tissue with said surgical instrument; and, removing said severed tissue from said internal body cavity via said tubular body.

11. A method for performing percutaneous surgery on a body, comprising the steps of:

insufflating an internal body cavity;

forming a first incision extending from an external body surface to said internal body cavity;

installing a modified gastrostomy device within said first incision, said modified gastrostomy device having a tubular mid-portion through which surgical instruments may be inserted into said internal body cavity;

forming a second incision extending from said external body surface to said internal body cavity;

positioning an entry port device within said internal body cavity, said entry port device having a tubular body with a bolster portion at one end and a dilator portion at an opposite end;

inserting said dilator portion into and through said second incision such that said dilator portion is on an exterior of the body, said tubular body having a portion which lies within said second incision and a portion which projects outwardly from said second incision while said bolster portion is in contact with an inner body surface surrounding said internal body cavity;

sliding an external bolster over said tubular body and against said external body surface;

severing said tubular body at a location adjacent said dilator portion;

inserting a first surgical instrument through said modified gastrostomy device and into said internal body cavity, said first surgical instrument having a tissue engaging portion within said internal body cavity and a user engageable portion projecting outwardly from said modified gastrostomy device;

inserting a second surgical instrument through said tubular body and into said internal body cavity, said second surgical instrument having a tissue engaging portion within said internal body cavity and a user engageable portion projecting outwardly from said tubular body;

adjusting said user engageable portions of said surgical instruments to manipulate said tissue engaging portions and thereby perform a surgical procedure within said internal body cavity.

12. A method for performing percutaneous surgery as recited in claim 11, comprising the further step of:

using a clamp to constrict the projecting portion of said tubular body to prevent pressurized air within said internal body cavity from flowing through said tubular body to atmosphere.

13. A method for performing percutaneous surgery as recited in claim 12, further comprising the steps of:

removing said clamp from said projecting portion of said tubular body;

inserting a first air flow control device into said tubular body to minimize leakage of pressurizing air through said tubular body; and, inserting a second air flow control device into said modified gastrostomy device to minimize leakage of pressurizing air through said modified gastrostomy device.

14. A method for performing percutaneous surgery as recited in claim 13, further comprising the steps of:

inserting an endoscope tube into the internal body cavity; and, remotely visualizing the surgical procedure being performed via the endoscope tube.

15. A method for performing percutaneous surgery as recited in claim 14, comprising the further steps of:

severing tissue with one of said first and second surgical instruments while holding said tissue with the other of said first and second surgical instruments; and, removing said severed tissue from said internal body cavity by withdrawing said other of said first and second surgical instruments from said internal body cavity.

16. A method for performing percutaneous surgery as recited in claim 11, comprising the further steps of:

severing tissue with one of said first and second surgical instruments while holding said tissue with the other of said first and second surgical instruments; and, removing said severed tissue from said internal body cavity by withdrawing said other of said first and second surgical instruments from said internal body cavity.

\* \* \* \* \*